United States Patent [19]

Varadaraj et al.

[11] Patent Number: 5,624,843
[45] Date of Patent: *Apr. 29, 1997

[54] NUTRIENT ADDITIVES FOR BIOREMEDIATION OF HYDROCARBON CONTAMINATED WATERS

[75] Inventors: Ramesh Varadaraj, Flemington; Jan Bock, Warren; Max L. Robbins, South Orange, all of N.J.

[73] Assignee: Exxon Research and Engineering Company, Florham Park, N.J.

[*] Notice: The term of this patent shall not extend beyond the expiration date of Pat. No. 5,436,160.

[21] Appl. No.: 395,217

[22] Filed: Feb. 27, 1995

Related U.S. Application Data

[63] Continuation-in-part of Ser. No. 190,391, Feb. 2, 1994, Pat. No. 5,436,160.

[51] Int. Cl.$^6$ .............................. C10G 32/00; C02F 3/00; C02F 3/36
[52] U.S. Cl. .................. 435/264; 435/262; 435/262.5; 435/281
[58] Field of Search ..................... 435/264, 262, 435/281, 262.5

[56] References Cited

U.S. PATENT DOCUMENTS

| 3,616,204 | 10/1971 | Linn | 435/281 |
|---|---|---|---|
| 4,146,470 | 3/1979 | Mohan et al. | 435/281 |
| 5,017,289 | 5/1991 | Guy et al. | 210/610 |
| 5,104,525 | 4/1992 | Roderick | 210/87 |
| 5,128,262 | 7/1992 | Lindoerfer et al. | 435/264 |
| 5,300,227 | 4/1994 | Varadaraj et al. | 210/610 |

*Primary Examiner*—Herbert J. Lilling
*Attorney, Agent, or Firm*—Joseph J. Dvorak

[57] ABSTRACT

The biodegradation of hydrocarbon contaminated water is enhanced by the adding to the contaminated water a hydrocarbon solution of (a) a mixture of a sorbitan ester of a $C_7$ to $C_{22}$ monocarboxylic acid and a polyoxyalkelene adduct of a sorbitan ester of a $C_7$ to $C_{22}$ monocarboxylic acid, the adduct having from 4 to 50 polyoxyalkelene units, (b) an alkyl glycoside wherein the alkyl group has from about 8 to 18 carbon atoms and the gylcoside is a mono or diglycoside, or a mixture thereof, in amounts sufficient to promote the growth of indigenous microorganisms.

In another embodiment of the invention a source of microbial assimilable nitrogen and phosphorous also is supplied to the contaminated water.

10 Claims, No Drawings

NUTRIENT ADDITIVES FOR BIOREMEDIATION OF HYDROCARBON CONTAMINATED WATERS

CROSS REFERENCE TO RELATED APPLICATION

This application is a continuation-in-part of U.S. Ser. No. 190,391 filed Feb. 2, 1994, now U.S. Pat. No. 5,436,160.

FIELD OF THE INVENTION

The present invention relates to microbial remediation of hydrocarbon contaminated waters, especially hydrocarbon contaminated water contained in treatment tanks and oily sludge holding ponds.

BACKGROUND OF THE INVENTION

Efficient biodegradation of hydrocarbon contaminants in hydrocarbon contaminated water treatment tanks and oily sludge holding ponds is of growing importance in remediation of industrial waste. Typically, the microbial degradation is facilitated by adding microbial nutrients such as nitrogen and phosphorous containing nutrients to the waters. Occasionally a microbial innoculum is also added. While nutrient addition is beneficial further enhancements in the rate and extent of biodegradation of the contaminants is still desirable. Enhanced rates leads to shorter holding times in the water treatment tanks. Enhanced extents or degrading the more recalcitrant contaminants, especially in sludge holding ponds, leads to higher contaminant removal and facilitates regulatory pond closures.

In the biodegradation of hydrocarbon contaminants, especially contaminants like petroleum distillate heavy ends and tank bottoms it appears that the rate and extent of microbial utilization of the contaminants is limited amongst other things by the number and activity of hydrocarbon assimilating micro flora.

Accordingly, it is an object of the present invention to provide an improved method for enhancing the biodegradation of hydrocarbons in water by stimulating the growth and activity of the hydrocarbon assimilating micro flora.

SUMMARY OF THE INVENTION

In one embodiment of the present invention, the biodegradation of hydrocarbon contaminated water is enhanced by the adding to the contaminated water a hydrocarbon solution of (a) a mixture of a sorbitan ester of a $C_7$ to $C_{22}$ monocarboxylic acid and a polyoxyalkelene adduct of a sorbitan ester of a $C_7$ to $C_{22}$ monocarboxylic acid, the adduct having from 4 to 50 polyoxyalkelene units, (b) an alkyl glycoside wherein the alkyl group has from about 8 to 18 carbon atoms and the gylcoside is a mono or diglycoside, or a mixture thereof, in amounts sufficient to promote the growth of indigenous micro organisms.

In another embodiment of the invention a source of microbial assimilable nitrogen and phosphorous are supplied to the contaminated water.

These and other embodiments of the present invention will be described in greater detailed description which follows.

DETAILED DESCRIPTION OF THE INVENTION

For sake of brevity, the present invention will be described in terms of enhancing the biodegradation of hydrocarbon contaminants in water in general. However, it should be understood that the invention is especially applicable to improving the bioremediation of contained bodies of hydrocarbon contaminated water such as that in water treatment tanks, sludge ponds and the like.

In the practice of the present invention, the bioremediation of hydrocarbon contaminated water is enhanced by adding to the contaminated water a hydrocarbon solution of an additive selected from the group consisting of: (a) a mixture of monocarboxylic acid esters of sorbitan and a polyoxyalkelene adduct of monocarboxylic acid esters of sorbitan (b) an alkyl glycoside and (c) a mixture of (a) and (b).in amounts sufficient to promote the growth of indigenous micro-organisms. Typically, the sorbitan carboxylic acids forming the esters will have from 7 to 22 carbon atoms; the polyoxyalkelene groups will range from 4 to 50 units per adduct and preferably will be selected from polyoxyethylene and polyoxypropylene groups; and in the case of alkyl glycosides, the alkyl groups will have from about 8 to 18 carbon atoms. Also, the glycoside is a mono or diglycoside or a mixture thereof.

In general, the mixture of additives is dissolved in a normal or branched aliphatic hydrocarbon having from 6 to 16 carbon atoms although hydrocarbons like tetralin, cycloalkanes, alkyl substituted aromatics and terpenes or alcohols like isopropyl alcohol may also be employed as a solvent.

The additives will constitute from about 15 to 85 wt % of the total weight of the solution. In a preferred embodiment of the present invention, the above solution is applied to the contaminated water at a rate from about 1 to 30 wt % of solution based on the weight of the hydrocarbon contaminant in the water.

In the practice of the present invention, it is especially preferred to supply the contaminated water with a source of microbial assimiable nitrogen and phosphorous.

Typical sources of microbial assimilable nitrogen and phosphorous will include urea, potassium phosphate, potassium nitrate, ammonium nitrate, ammonium phosphate and the like. In general these nutrients are added at a rate to provide a carbon to nitrogen to phosphorous ratio in the range of about 100:1:0.1 to about 100:10:5 and preferably 100:4:0.4. In general, these nutrients will be supplied to the contaminated water after adding the hydrocarbon additive solution. However, the time of supply is not critical and the nutrients optionally can be added first or simultaneously as well.

It is preferred to mix the contaminated waters and additive solution to provide better contact between them and also provide aeration for microbial action. Aeration may also be provided by bubbling air into the contaminated water.

Hydrocarbon degrading micro flora are most often present in waste water treatment tanks and oily sludge holding ponds. Nonetheless, it is preferred to determine the existence of these microbes and in the event of their absence, it is preferred to inoculate the contaminated waters with hydrocarbon degrading microbes. Typical innoculum size is about 0.1 to 1 wt % of the amount of water.

EXAMPLES

In the following examples 300 ml Wheaton 4-baffle glass flasks were used. A vibrating shaker table shaken at 200 rpm provided the mixing and aeration. The test hydrocarbon was a 520–1050° F. distillation fraction of Alaskan north slope crude oil. The test formulation constituted 62 wt % additives of the invention and 38 wt % solvent. The solvent was Norpar-13, which is the trademark for a relatively narrow boiling range solvent sold by Exxon Company U.S.A., Houston, Tex. Norpar-13 contains greater than 98 wt % on normal paraffins. The additive was a 3:1 mixture of sorbitan monololeate and polyoxyethylene (20) sorbitan monooleate. The sorbitan monooleate and the polyoxyethylene (20) sorbitan monooleate are sold under the trade names Span 80 and Tween 80 by ICI Americas, Wilmington, Del. The Freon (trademark of DuPont de Nemours) used was 1,1,2-trichloro-1,2,2-trifluroethane.

Example 1

To 0.5 g of the test oil was mixed 0.050 g of the test formulation and the mixture added to 45 ml of water. The water was a H44 mineral media which is a standard mineral media for micro biological test assays. Microbial nitrogen and phosphorous nutrients, urea and ammonium phosphate were added to the flask to attain a C:N:P ratio of 100:3.7:0.08. A 5 ml bacterial innoculum obtained from a refinery biological waste water treatment unit was then added to the flask and the stirring commenced. The flasks were set up in triplicate. After 48 hours, the biodegradation was stopped by addition of 20 ml of Freon to the flasks. The undegraded oil was extracted by the standard liquid-liquid extraction technique using Freon as the solvent. EPA method 418.1 (infrared spectrometry) was used to determine the amount of residual oil and the % biodegradation was determined by difference. The amount of biomass generated in the experiment was determined by filtration of the aqueous phase and gravimetric estimation. The biomass is expressed as grams of biomass per gram of added oil. The results are given in the Table which follows along with results for the Comparative Examples.

Comparative Examples 1 and 2

In comparative example 1, the flasks were set up and run under identical conditions described in Example -1 above with urea and ammonium phosphate but without the additive. This served as a measure of the influence of microbial nutrients on biodegradation of the test oil.

In comparative example 2, the flasks were set up and run under identical conditions described in Example-1 above with no additive or microbial nutrients. This served as a measure of the influence of the water and innoculum effects on biodegradation of the test oil.

For both comparative examples the analysis techniques were identical to the one used for Example-1.

The results are given in Table below.

TABLE

| Example | Additive/ Nutrients | % Biodegraded | g biomass/g oil |
| --- | --- | --- | --- |
| Example 1 | This Invention | 50.2 | 0.30 |
| Comparative Ex. 1 | Nutrients Only | 36.5 | 0.14 |
| Comparative Ex. 2 | None | 10.0 | <0.01 |

What is claimed is:

1. A method for improving the bioremediation of hydrocarbon contaminated water with indigenous microorganisms comprising adding to the hydrocarbon contaminated water a hydrocarbon solution of an additive selected from the group consisting of (a) a mixture of a sorbitan ester of a $C_7$ to a $C_{22}$ monocarboxylic acid and a polyaxyalkylene adduct of a sorbitan monoester of a $C_7$ to $C_{22}$ monocarboxylic acid, the adduct having from 6 to 50 polyoxyalkylene units, (b) an alkylglycoside wherein the alkyl group has from about 8 to 18 carbon atoms and the glycoside is a mono or a diglycoside, and (c) a mixture of (a) and (b), the solution being added in amounts sufficient to promote the growth of indigenous micro organisms.

2. The method of claim 1 wherein the additive constitutes from about 15 to about 85 weight % of the total solution.

3. The method of claim 2 wherein the hydrocarbon solvent is selected from linear and branched hydrocarbons having from 6 to 16 carbon atoms, tetraline, cycloalkanes, alkyl substituted aromatics, terpene and alcohols.

4. The method of claim 3 wherein the hydrocarbon solution is added at a rate of from about 1 to about 30 wt. % based on the weight of hydrocarbon containment in the water.

5. The method of claim 4 including supplying the water with a source of microbial assimilable nitrogen and phosphorous.

6. The method of claim 5 wherein the source of nitrogen and phosphorous is added in an amount to provide a C:N:P ratio in the range of from about 100:1:0.1 to about 100:10:5.

7. The method of claim 6 including mixing the contaminated water and hydrocarbon solution.

8. In the bioremediation of contained bodies of hydrocarbon contaminated water with indigenous micro organisms the improvement comprising:

adding to the hydrocarbon contaminated water (1) a hydrocarbon solution of an additive selected from the group consisting of (a) a mixture of a sorbitan ester of a $C_7$ to a $C_{22}$ monocarboxylic acid and a polyaxyalkylene adduct of a sorbitan monoester of a $C_7$ to $C_{22}$ monocarboxylic acid, the adduct having from 6 to 50 polyoxyalkyline units, (b) an alkylglycoside wherein the alkyl group has from about 8 to 18 carbon atoms and the glycoside is a mono or a diglycoside, and (c) a mixture of (a) and (b), the solution being added in amounts sufficient to promote the growth of indigenous micro organisms and (2) a source of microbial assimilable nitrogen and phosphorous in an amount to provide a C:N:P ratio of from about 100:1:0.1 to about 100:10:5 whereby the bioremediation of the contaminated water is enhanced.

9. An improved method for bioremediation of hydrocarbon contaminated water contained in water treatment tanks and sludge ponds comprising:

adding to the contaminated water a hydrocarbon solution of an additive selected from the group consisting of (a) a mixture of a sorbitan ester of a $C_7$ to a $C_{22}$ monocarboxylic acid and a polyaxyalkylene adduct of a sorbitan monoester of a $C_7$ to $C_{22}$ monocarboxylic acid, the adduct having from 6 to 50 polyoxyalkyline units, (b) an alkylglycoside wherein the alkyl group has from about 8 to 18 carbon atoms and the glycoside is a mono or a diglycoside, and (c) a mixture of (a) and (b), the solution being added in amounts sufficient to promote the growth of indigenous micro organisms and (2) a source of microbial assimilable nitrogen and phosphorous in an amount to provide a C:N:P ratio of from about 100:1:0.1 to about 100:10:5 whereby the bioremediation of the contaminated water is enhanced and thereafter mixing the water and hydrocarbon solution.

10. The method of claim 9 wherein the hydrocarbon solution contains from about 15 to about 85 wt % of the total weight of solution and is added at a rate of from about 1 to about 30 wt % based on the total weight of the hydrocarbon contaminant in the water.

* * * * *